United States Patent [19]

Anderson, II et al.

[11] Patent Number: 5,981,283
[45] Date of Patent: Nov. 9, 1999

[54] METHOD OF TAGGING HYDROCARBON FUELS

[75] Inventors: David K. Anderson, II, Houston; Manuel E. Gonzalez; Nicholas Paul Valenti, both of Kingwood, all of Tex. 77339

[73] Assignee: Isotag, L.L.C., Houston, Tex.

[21] Appl. No.: 08/571,361

[22] Filed: Dec. 12, 1995

Related U.S. Application Data

[63] Continuation-in-part of application No. 08/108,625, filed as application No. PCT/US93/00647, Jan. 25, 1993, Pat. No. 5,474,937, which is a continuation-in-part of application No. 07/825,478, Jan. 29, 1992, abandoned.

[51] Int. Cl.[6] .................................................. G01N 33/24
[52] U.S. Cl. .............................. 436/27; 436/56; 436/141; 436/60; 436/161
[58] Field of Search .................................. 436/56, 3, 22, 436/141, 161, 60

[56] References Cited

U.S. PATENT DOCUMENTS

| | | | |
|---|---|---|---|
| 1,997,670 | 4/1935 | Armour | 44/9 |
| 2,392,620 | 1/1946 | Sparks | 250/71 |
| 2,689,171 | 9/1972 | Hager | 23/230 |
| 3,704,952 | 12/1972 | Bird | 356/87 |
| 3,764,273 | 10/1973 | Turner et al. | 23/230 R |
| 3,861,886 | 1/1975 | Meloy | 44/51 |
| 3,883,568 | 5/1975 | Turner et al. | 260/283 |
| 3,964,294 | 6/1976 | Shair et al. | 73/53 |
| 4,514,503 | 4/1985 | Orelup | 436/60 |
| 4,520,109 | 5/1985 | Simmonds et al. | 436/56 |
| 4,764,474 | 8/1988 | Orelup | 436/111 |
| 5,244,808 | 9/1993 | Nowak | 436/56 |
| 5,279,967 | 1/1994 | Bode | 436/56 |
| 5,304,493 | 4/1994 | Nowak | 436/56 |

*Primary Examiner*—Lyle A. Alexander

[57] ABSTRACT

A liquid hydrocarbon fuel composition comprises at least one tagging agent and a mixture of hydrocarbon components having boiling points in the range of about 100 degrees F. to about 800 degrees F. The tagging agent is present at a concentration in the range of from about 0.5 ppb to about 500 ppb. The tagging agent is elutable by chromatographic analysis of the liquid hydrocarbon fuel composition apart from the hydrocarbon components of the fuel composition. The tagging agent is formed from an organic compound containing elements found at natural isotopic abundance. Preferably, two or more tagging agents are employed in the fuel so that each fuel composition can be assigned a unique tagging agent composition. Analysis techniques are also disclosed.

7 Claims, No Drawings

METHOD OF TAGGING HYDROCARBON FUELS

This application is a continuation-in-part of application Ser. No. 08/108,625, now U.S. Pat. No. 5,474,937 filed under 35 USC § 371 on Aug. 30, 1993 from PCT application Ser. No. PCT/US93/00647, filed Jan. 25, 1993 and claiming priority as a continuation-in-part from U.S. application Ser. No. 07/825,478, filed Jan. 29, 1992, now abandoned.

BACKGROUND OF THE INVENTION

There is a long felt and unsolved need by the petroleum industry for economical techniques to serialize petroleum products such as liquid hydrocarbon fuels for internally auditing the transfer of such products to prevent and/or prove theft and/or counterfeiting.

There is also a long felt and unsolved need by the petroleum industry to be able to determine when a distributor has sold an inexpensive liquid hydrocarbon fuel as an expensive liquid hydrocarbon fuel or has used an inexpensive liquid hydrocarbon fuel to dilute an expensive fuel. For example, a low octane gasoline product may be used to dilute a high octane gasoline product, winter gasoline may be used to dilute summer gasoline, high altitude gasoline may be used to dilute low altitude gasoline, low oxygenate gasoline may be used to dilute high oxygenate gasoline, and high aromatics content gasoline may be used to dilute low aromatics content gasoline. On the diesel fuel side, No. 2 diesel may be used to dilute No. 1 diesel, railroad diesel may be used to dilute No. 2. diesel, high aromatics content diesel may be used to dilute low aromatics content diesel, and high sulfur diesel may be used to dilute low sulfur content diesel. Similar situations exist for kerosenes and jet fuels. Any of these occurrences can lead to unjustified liability for the refiner.

There is also a long felt and unsolved need by the government to be able to determine whether applicable taxes have been paid on hydrocarbon fuels, and whether tax exempt fuels are being sold as tax paid fuels or being used to dilute tax paid fuels. As an example, diesel fuel for road use is taxed at a higher rate than diesel fuel for off road use. There is also a long felt and unsolved need by the government for safe technique for "serializing" or "fingerprinting" petroleum products such as liquid hydrocarbon fuels so that responsibility for dumping, spilling or leakage of such fuels can be appropriately determined.

Efforts have been made in the past to tag the lower value products with various dyestuffs to enable the detection of their use to dilute a higher value product not containing the dyestuff. However, the number of suitable dyestuffs is limited and the dyestuffs are relatively expensive. Also, because the dyestuffs are visible, they can be counterfeited. Further, the technique of using the dyestuffs is not well suited for determining when a dyed product has been diluted with an undyed product. As an additional problem, when a pipeline is used to carry multiple products, the product which follows a dyed product can become contaminated with the dye. This can cause the product which follows to be rejected by the purchaser for failing to meet specifications.

The problem is exacerbated by the sheer number of liquid hydrocarbon products available which can be used to dilute another liquid hydrocarbon product. Gary et. al, "Petroleum Refining, Technology and Economics", 1975 LCCCN 75-18784, indicates on page 6 that the U.S. Petroleum Industry makes 19 motor gasoline products, 9 aviation gasoline products, 5 other gasoline products, 5 jet fuel products, 10 kerosine products, and 27 diesel fuel and light fuel oil products. With tighter emissions standards, the number is doubtless higher now.

A tagging system to enable the refiner to determine when its products have been used to dilute other products or sold in the place of such other products would be very desirable. A tagging system to enable governmental bodies determine when tax paid products have been diluted and the amount of such dilution or when untaxed or low taxed products are sold in the place of tax paid products would be very desirable. A tagging system to enable governmental bodies to determine when a fuel which meets environmentally mandated specifications has been diluted with product which does not meet such specifications would also be very desirable.

SUMMARY OF THE INVENTION

In certain embodiments of the invention, there is provided a method for labeling a fluid with an integral custody tag. The method is carried out by dispersing a detectable amount of the custody tag in the fluid. The custody tag is characterized in that it contains at least two tagging agents. When the tagging agents employed are selected from a moderately sized collection of tagging agents, the use of two or more tagging agents makes possible a very large number of unique custody tag possibilities.

In another embodiment of the invention there is provided a method for analyzing a fluid to determine the identity of any tagging agents contained therein. The method is carried out by obtaining a sample of the fluid. The sample is converted into a chromatograph stream, such as by introduction into a gas chromatograph. The method is characterized in that a plurality of portions of the chromatograph streams are trapped and analyzed for the presence or absence of tagging agents. The method is further characterized in that the plurality of portions which are so trapped are predetermined. The predetermination is easily done when it is known that the tagging agents have been selected from a moderately sized collection of tagging agents. The portions of the stream which are trapped are simply those which may contain one of the constituents of the collection.

In a further embodiment of the invention, there is provided a method of relabeling a fluid which is known to contain a custody tag comprising at least two tagging agents. The method comprises dispersing a custody tag modifier into the liquid to form a relabeled fluid. The custody tag modifier contains at least one tagging agent. Preferably, the tagging agent in the modifier is different from the two tagging agents in the liquid to be relabeled.

In a further embodiment of the invention, there is provided a method of tagging a liquid hydrocarbon bulk material comprising a mixture of different components. The liquid hydrocarbon bulk material to be tagged elutes from a chromatograph as a chromatograph stream formed by slugs of the different components in a carrier fluid flow. The chromatograph stream is separable into elution time windows containing slugs of the different components and elution time windows consisting essentially of carrier fluid flow. Each of the elution time windows has a characteristic spectrum indicative of the molecular identities of the components in the elution time window when process by an analytical technique for determining molecular identity, such as mass spec. The mass spec is composed of a plurality of mass spectrum peaks. The method comprises providing in such liquid hydrocarbon bulk material a quantity of a chemical component. The chemical component is soluble in the liquid hydrocarbon bulk material and elutes from a chromatograph stream formed from a sample of the liquid hydrocarbon bulk material containing the chemical component in a predetermined elution time window. The chemical component has at least one peak in its characterizing spectrum which is different from any other peak due to a component in the hydrocarbon material in the elution time window with such chemical component elutes.

In a further embodiment of the invention, there is provided a method for determining that a first liquid hydrocarbon bulk material has been blended with a second liquid hydrocarbon bulk material to form a third liquid hydrocarbon bulk material. Each of the liquid hydrocarbon bulk materials comprises a mixture of different components and elutes from a chromatograph as a chromatograph stream formed by slugs of the different components in a carrier fluid flow. The chromatograph stream is separable into elution time windows containing slugs of the different components and elution time windows consisting essentially of carrier fluid flow. Each of the elution time windows has a characteristic mass spectrum composed of a plurality of mass spectrum peaks. The method comprises adding to the first liquid hydrocarbon bulk material a known quantity of a first chemical component which is soluble in the first liquid hydrocarbon bulk material. The first chemical component elutes from a chromatograph stream formed from a sample of the first liquid hydrocarbon bulk material containing the first chemical component in a predetermined elution time window. The first chemical component has at least one mass spectrum peak which is different from any mass spectrum peak in the elution time window with such first chemical component elutes. A chromatographic/mass spec analysis of the first liquid hydrocarbon material is performed. A first mass spec signal representative of the concentration of the first chemical component added to the first liquid hydrocarbon material is obtained. A chromatographic/mass spec analysis of the third liquid hydrocarbon material is performed. A second mass spec signal representative of a lower concentration of the first chemical component in the third liquid hydrocarbon material is obtained.

In another embodiment of the invention, there is provided a liquid hydrocarbon fuel composition. The liquid hydrocarbon fuel composition comprises at least one tagging agent and a mixture of hydrocarbon components having boiling points in the range of about 100 degrees F. to about 800 degrees F. The tagging agent is present at a concentration in the range of from about 0.5 ppb to about 500 ppb. The tagging agent is elutable by chromatographic analysis of the liquid hydrocarbon fuel composition apart from the hydrocarbon components of the fuel composition. The tagging agent is formed from an organic compound containing elements found at natural isotopic abundance.

In another embodiment of the invention, there is provided a liquid hydrocarbon fuel composition. The liquid hydrocarbon fuel composition comprises a mixture of hydrocarbon components having boiling points in the range of about 100 degrees F. to about 800 degrees F. The composition contains a tagging agent at a concentration in the range of from about 0.5 ppb to about 500 ppb. The tagging agent is elutable by chromatographic analysis of the liquid hydrocarbon fuel composition apart from most of the hydrocarbon components of the fuel composition. The tagging agent is formed from an organic compound containing elements found at natural isotopic abundance. The tagging agent has a mass spec which contains a peak which is different from any peak from a hydrocarbon component of the fuel composition with which the tagging agent elutes.

In another embodiment of the invention, there is provided a process for adding a tagging agent to a liquid hydrocarbon fuel. The tagging agent is added in a process comprising metering an additive package into a liquid hydrocarbon fuel composition. The improvement comprises incorporating a tagging agent into an additive package for the liquid hydrocarbon fuel composition. The tagging agent is formed from an organic compound containing elements at natural isotopic abundance selected from the group consisting of carbon, hydrogen, oxygen, nitrogen, sulfur and halogen. The tagging agent is incorporated in the additive package at a concentration sufficient to impart to the liquid hydrocarbon fuel composition a concentration of the tagging agent in the range of from about 0.5 ppb to about 500 ppb.

DETAILED DESCRIPTION OF THE INVENTION

In certain embodiments of the invention, fluid compositions can be labeled or tagged by incorporating custody tag or custody tag modifiers therein.

The fluid compositions are generally gases or liquids. The liquids are generally classified as oil based or water based. Oil based liquids generally include petroleum, and petroleum products. Volatile custody tags and custody tag modifiers are used to tag gases. Oil soluble custody tags and custody tag modifiers are generally used to tag oil based liquids. Water soluble custody tags and custody tag modifiers are generally used to label water based liquids. The custody tags are integral with the fluids and are nearly impossible to remove.

The invention is especially applicable to the tagging of liquid hydrocarbon bulk materials, especially liquid fuels, and the components, such as naphtha, which are blended to form liquid fuels. The term liquid hydrocarbon bulk materials is intended to encompass both fuels and fuel components. Such fuels generally comprise a mixture of hydrocarbon components having boiling points in the range of about 100 degrees F. to about 800 degrees F. For example, the invention can be used to tag gasoline, diesel fuel, kerosene and jet fuel with good results, as well as used to tag fuel oils and bunker fuels, or the components which are blended together to form these fuels.

Generally speaking, the tagging agent will be selected to elute separately from the fuel components of the composition when the composition is subjected to chromatographic analysis. In chromatographic analysis, the liquid hydrocarbon material elutes from the chromatograph as a chromatograph stream formed by slugs of the different components in a carrier fluid flow. The chromatograph stream is separable into elution time windows containing slugs of the different components and elution time windows consisting essentially of carrier fluid flow. The elution time windows are processed by an analytical technique for determining molecular identity. Preferably, the technique is mass spectroscopy and each elution time window has a characteristic mass spectrum composed of a plurality of mass spectrum peaks.

The tagging agent is provided in the liquid hydrocarbon bulk material in the form of a quantity of a chemical component which is soluble in the liquid hydrocarbon bulk material and elutes from a chromatograph stream formed from a sample of the liquid hydrocarbon bulk material containing the chemical component in a predetermined elution time window. The chemical component has at least one mass spectrum peak which is different from any mass spectrum peak due to the bulk material in the elution time window with such chemical component elutes.

This can be accomplished by selecting a tagging agent which has a boiling point outside of the boiling range of the fuel. It can also be accomplished by selecting a tagging agent which has a boiling point within the range of the fuel, but which elutes in a separate elution time window apart from any fuel components. It can also be accomplished by selecting a tagging agent which elutes together with fuel components but which has a characterizing spectral property so that its presence can be quantitatively distinguished from the fuel components. For example, the tagging agent can be selected so that it has at least one mass spectrum peak which is different from any mass spectrum peak due to any of the fuel components with which it has eluted. As another example, a halogenated tagging agent could be employed and its presence in the elution time window could be quantified using an electron capture detector.

The amount of custody tag or tag modifier incorporated into the fluid can vary over a wide range. However, the tagging agent should always be added in an amount sufficient to be detected in the tagged product. Often, the custody tag will be used in a liquid hydrocarbon fuel at below the 500 ppb level. In many instances, a concentration of custody tag in the range of 0.5 to 500 ppb will give desirable results. A concentration of custody tag in the range of 10 ppb and 100 ppb has been tested with good results.

The custody tag can be added to the fluid using a variety of techniques, depending on how well dispersion is expected. For example, the custody tag can be metered into a stream as it flows through a line, such as by being metered into a hydrocarbon stream together with an additive package. This will generally provide a better result than simply dumping the custody tag into a large storage tank, for example. However, an fuel tanker can be treated by pouring the custody tag in the hold and then filling the tanker with fuel. It is preferred to add the custody tag continuous to the fluid through a metering system at a transfer or storage facility.

Generally speaking, a custody tag will comprise at least two tagging agents, preferably three or more. Custody tag modifiers comprise at least one tagging agent, preferably only one. A custody tag modifier can be used to relabel a fluid containing a custody tag to indicate, for example, a transfer of custody. Preferably, the tagging agent present in a custody tag modifier is different from any of the tagging agents in the custody tagged fluid being relabeled.

Preferred tagging agents are organic compounds, preferably those which are compatible in small amounts with the intended use of the fuel and are soluble in the fuel in at least small amounts. Preferred compounds may contain O, N, S or halogen in addition to C and H, since such elements are normally found in hydrocarbon fuels. Preferably, all elements contained in the tagging agent are found at natural isotopic abundance, since the elements are found in the fuel at natural isotopic abundance. The tagging agents are employed in sufficiently small amounts that their presence is not detectable in the bulk material without the use of sensitive analytic instruments, and not easily detectable even with analytic instruments unless their identity is known. Suitable materials are generally oleophilic and hydrophobic, since the fuel compositions are generally oleophilic and hydrophobic.

Tagging agents suitable for use can generally be described as non-radioactive compounds. Preferably, the tagging agents used can be detected in the fluid which contains them at concentrations of less than 500 ppb, such as in the 0.5–500 ppb range.

It is desirable to assemble a library or collection of suitable tagging agents and make selections from the library to formulate custody tags based on compatibility of the tagging agents with the fluid to be tagged and the use of a unique tag.

Two classes of suitable materials which can be used as tagging agents are polynuclear aromatic hydrocarbons and halogenated hydrocarbons. Examples of suitable tagging agents include 1,2-diphenylbenzene; 1,4-diphenylbenzene, triphenylmethane, 1,3,5-triphenylbenzene, 1,1,2-triphenylethylene; tetraphenylethylene, 1,2,3,4-tetrahydrocarbazole, 1,3-diphcnylacetone, 2-chlorobenzophenone; 4,4'-dichlorobenzophenone; 4-benzoylphenone; 4-bromobenzophenone; 4-methoxybenzophenone; 4-methylbenzophenone; 9-fluorenone; 1-phenylnaphthalene; 3,3'dimethoxybiphenyl; and 9-phenylanthracene.

Compatibility is rather easy to determine and is based on the range of properties of the fluid to be transported or stored. It does not require an especially large collection of tagging agents to accomplish the capability to provide unique combinations. For example, 1,000 tagging agents can be used to formulate over 41 billion unique 3-component custody tags.

The presently preferred analysis technique for the detection of tagging agents utilizes a gas chromatograph coupled with a mass spectrometer although other chromatographic and detection techniques can be used as well. It is first necessary, of course, to obtain a sample of the material to be analyzed for the presence of tagging agents. The sample is formed into a gas chromatograph stream and the stream is then flowed through the gas chromatograph. Predetermined portions of the stream are trapped and analyzed for tagging agent. Generally speaking, the analysis is carried out with a mass spectrometer. For difficult separations, the trapped portions of the sample are formed into a second stream and flowed through a second gas chromatograph. Predetermined portions of the second gas stream are trapped and analyzed for tagging agent. The determination of which portions of the chromatograph stream to trap is generally made before the original analysis of the sample and is usually based on retention time. It is made using knowledge of the tagging agent collection from which the tagging agents were selected, sometimes after a calibration run using known combinations of tagging agents from the collection.

EXAMPLE 3.2 Kg of a chemical tag was added to a 14,000 gallon container of gasoline additive.

The chemical tag was o-terphenyl. A previous chemical analysis of the gasoline intended to be tagged had revealed the absence of o-terphenyl at detection limits.

The additive was metered into the gasoline product at the ratio of ½ gallon of additive per 1,000 gallons of gasoline.

The resulting concentration of the chemical tag in the gasoline product into which the additive has been metered was calculated to be 40 ppb. This was confirmed by chemical analysis.

The objective of the tagging was to determine the amount of dilution that the tagged gasoline experiences as a result of being mixed with untagged gasoline after it leaves the refiner's possession. Analysis of the gasoline at the gas station pump would reveal a concentration of o-terphenyl of 40 ppb unless the gasoline had been diluted by another product.

Having described the invention above, various modifications of the techniques, procedures, material and equipment will be apparent to those in the art. It is intended that all such variations within the scope and spirit of the appended claims be embraced thereby.

We claim:

1. A method of tagging a liquid hydrocarbon bulk material comprising a mixture of components, wherein the components of said liquid hydrocarbon bulk material elute from a gas chromatograph as a gas chromatograph stream composed of elution time windows containing components of the mixture and elution time windows consisting essentially of carrier gas flow; each such elution time window of the gas chromatograph stream having a characteristic mass spectrum indicative of the molecular identities of the components in the elution time window when processed by mass spectrometer;

said method comprising providing in such liquid hydrocarbon bulk material a quantity of a chemical component which is soluble in said liquid hydrocarbon bulk material and elutes from a gas chromatograph in a predetermined elution time window of a gas chromatograph stream formed from a sample of the liquid hydrocarbon bulk material containing the chemical component, said chemical component having at least one peak in its characterizing mass spectrum which is different from any other mass spectrum peak in the predetermined elution time window which is due to any component of the liquid hydrocarbon bulk material which may be present in the predetermined elution time window.

2. A method as in claim 1 wherein the chemical component is an organic compound containing elements found at natural isotopic abundance.

3. A method as in claim 2 wherein the chemical component in provided in such liquid hydrocarbon bulk material at a concentration in the range of 0.5 ppb to 500 ppb.

4. A method as in claim 3 further comprising providing in the liquid hydrocarbon bulk material a second such chemical component which elutes from the gas chromatograph in a second predetermined elution time window.

5. A method for determining that a first liquid hydrocarbon bulk material has been blended with a second liquid hydrocarbon bulk material to form a third liquid hydrocarbon bulk material, each such liquid hydrocarbon bulk material comprising a mixture of components, wherein each liquid hydrocarbon bulk material elutes from a chromatograph as a chromatograph stream composed of elution time windows containing components of the mixture and elution time windows consisting essentially of carrier fluid flow; each such elution time window having a characteristic mass spectrum composed of a plurality of mass spectrum peaks;

said method comprising adding to the first liquid hydrocarbon bulk material a known quantity of a first chemical component which is soluble in said first liquid hydrocarbon bulk material and elutes from a chromatograph in a predetermined elution time window of a chromatograph stream formed from a sample of the first liquid hydrocarbon bulk material containing the first chemical component, said first chemical component having at least one mass spectrum peak which is different from any mass spectrum peak in the predetermined elution time window which is due to any component of the first liquid hydrocarbon bulk material, performing a chromatographic/mass spec analysis of the first liquid hydrocarbon material containing the first chemical component and obtaining a first mass spec signal representative of the concentration of the first chemical component added to the first liquid hydrocarbon material; and performing a chromatographic/mass spec analysis of the third liquid hydrocarbon material and obtaining a second mass spec signal representative of a lower concentration of the first chemical component in the third liquid hydrocarbon material.

6. A method as in claim 5 further comprising adding to the second liquid hydrocarbon bulk material a known quantity of a second chemical component which is soluble in said second liquid hydrocarbon bulk material and elutes from a chromatograph in a predetermined elution time window of a chromatograph stream formed from a sample of the second liquid hydrocarbon bulk material containing the second chemical component, said second chemical component having at least one mass spectrum peak which is different from any mass spectrum peak in the predetermined elution time window which is due to any component of the second liquid hydrocarbon bulk material, performing a chromatographic/mass spec analysis of the second liquid hydrocarbon material containing the second chemical component and obtaining a third mass spec signal representative of the concentration of the second chemical component added to the second liquid hydrocarbon material; and obtaining from the chromatographic/mass spec analysis of the third liquid hydrocarbon material a fourth mass spec signal representative of a lower concentration of the second chemical component in the third liquid hydrocarbon material.

7. A method as in claim 6 wherein the first chemical component elutes in a different predetermined elution time window than the second chemical component and the chromatograph is a gas chromatograph.

* * * * *